US00PP08345P

United States Patent [19]

VandenBerg

[11] Patent Number: Plant 8,345

[45] Date of Patent: Aug. 10, 1993

[54] CHRYSANTHEMUM PLANT NAMED RED DELANO

[75] Inventor: Cornelis P. VandenBerg, Salinas, Calif.

[73] Assignee: Yoder Brothers, Inc., Barberton, Ohio

[21] Appl. No.: 743,280

[22] Filed: Aug. 9, 1991

[51] Int. Cl.[5] ..... A01H 5/00

[52] U.S. Cl. ..... Plt./82

[58] Field of Search ..... Plt./76, 82, 82.5, 74.1

[56] References Cited

U.S. PATENT DOCUMENTS 4,616,099 10/1986 Sparkes ..... 47/58

OTHER PUBLICATIONS

Gosling, ed., 1979, "The Chrysanthemum Manual-6th edition", The National Chrysanthemum Society, London, Essex Telegraph Press, Ltd. pp. 329-336.

Broertjes, et al., 1978, "Application of Mutation Breeding Methods in the Improvement of Vegetatively Propagated Crops", Elsevier Sci. Pub. Co., New York, pp. 162-175.

Broertjes et al., 1980, "A mutant of a mutant of a . . . Irradiation of progressive radiation-induced mutants in a mutation breeding programme with *C. morifolium*", Euphytica, 29:526-530.

Searle, et al., 1968, "Chrysanthemums The Year Round", Blanford Press, London, pp. 27-29, 320-327.

Chan, 1966, "Chrysanthemum and rose mutations induced by X-rays", Am. Soc. Hort. Sci. Proc., pp. 613-620.

Broertjes, 1966, "Mutation breeding of Chrysanthemums", Euphytica, 15:156-162.

Dowrick et al., 1966, "The induction of mutation in Chrysanthemum using X-and gamma radiation", Euphytica, 15:204-210.

*Primary Examiner*—Howard J. Locker

*Attorney, Agent, or Firm*—Foley & Lardner

[57] ABSTRACT

A Chrysanthemum plant named Red Delano particularly characterized by its flat capitulum form; decorative capitulum type; dary red ray floret color; diameter across face of capitulum of 110 to 127 mm when fully opened, when grown as a pinched disbudded pot mum; photoperiodic flowering response to short days of 53 to 56 days; plant height, with 15 to 16 long days after sticking unrooted cuttings, and with 2 applications of 2500 ppm B-9 SP, ranges from 23 to 25 cm when grown as a pinched pot mum with 4 cuttings in a 15 cm pot; branching pattern is spreading and prolific, each plant having 4 to 5 laterals after pinch; and recommended as disbudded pot mum.

1 Drawing Sheet

The present invention comprises a new and distinct cultivar of Chrysanthemum, botanically known as *Dendranthema grandiflora,* and referred to by the cultivar name Red Delano.

Red Delano, identified as 5214 (84-258C06), is a product of a mutation induction program. The new cultivar was discovered and selected by Cornelis P. VandenBerg on Nov. 15, 1988 in a controlled environment in Salinas, Calif., as one flowering plant within a flowering block established as rooted cuttings from stock plants which had been exposed as unrooted cuttings to an X-ray source of 1500 rads in Fort Myers, Fla., on Apr. 28, 1988. The irradiated parent cultivar was the cultivar identified as Delano, disclosed in U.S. Plant Pat. No. 6,950, and described as a decorative disbud pot mum with a flat capitulum form; a dark red-purple ray floret color; diameter across face of capitulum of 120 to 140 mm when fully opened; flowering response period of 53 to 61 days after start of short days; plant height of 23 to 33 cm with 1 to 3 applications of 2500 ppm B-9 SP when grown as a pinched pot mum in a 15 cm pot; and spreading and prolific branching pattern, with 4 to 5 laterals after pinch.

The irradiation program resulting in Red Delano had as its primary objective the expansion of color ranges of the parent cultivar Delano. The irradiation program comprised irradiating cuttings of the parent cultivar at irradiation levels of 1500, 1750 and 2000 rads. A total of 588 cuttings harvested from a total of 225 irradiated plants were planted on September 19 and October 3 for 1500 rads treatment, and on September 12 and September 5 for the 1750 and 2000 rads treatment, respectively. Of these, 9 initial selections were made, which selections were then revegetated and reflowered. Three consecutive flowerings resulted in discarding 6 of the original 9 selections on Jul. 25, 1989. Three selections were retained as an "active" status and trialed for one year, ultimately resulting in discarding two of these three remaining selections, and the decision to introduce the one remaining selection as Red Delano.

The first act of asexual reproduction of Red Delano was accomplished when vegetative cuttings were taken from the initial selection in January 1989 in a controlled environment in Salinas, Calif., by technicians working under supervision of Cornelis P. VandenBerg. Horticultural examination of controlled flowerings of successive plantings has shown that the unique combination of characteristics as herein disclosed for Red Delano are firmly fixed and are retained through successive generations of asexual reproduction.

Red Delano has not been observed under all possible environmental conditions. The phenotype may vary somewhat with variations in environment such as temperature, light intensity and daylength, without, however, any variance in the genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Red Delano, which, in combination, distinguish this Chrysanthemum as a new and distinct cultivar:

1. Flat capitulum form.
2. Decorative capitulum type.
3. Dark red ray floret color.
4. Diameter across face of capitulum of 110 to 127 mm when fully opened, when grown as a pinched disbudded pot mum.
5. Photoperiodic flowering response to short days of 53 to 56 days.
6. Plant height, with 15 to 16 long days after sticking unrooted cuttings, and with 2 applications of 2500 ppm B-9 SP, ranges from 23 to 25 cm when grown as a pinched pot mum with 4 cuttings in a 15 cm pot.
7. Branching pattern is spreading and prolific, each plant haivng 4 to 5 laterals after pinch.
8. Recommended as disbudded pot mum.

The accompanying photographic drawing is a side view of a potted mum of Red Delano, with 4 cuttings in a 15 cm pot, with the colors being as nearly true as possible with illustrations of this type.

Of the commercial cultivars known to the inventor, the most similar in comparison to Red Delano is the parent cultivar Delano. All traits of Red Delano are similar to those of Delano, except for the ray floret color. Delano has very dark red-purple ray floret color, while Red Delano has a dark red ray floret color. In one of our flowering trials it was noted that Red Delano had a slightly smaller diameter of capitulum than Delano. When comparing the description of Red Delano with that of Delano, it is evident that Delano has a wider range for many characteristics than Red Delano. The reason for this is that the description of Delano is based on evaluations over a 3 year time period, while the description of Red Delano is based on considerably less flowerings in approximately one year time period.

In the following description color references are made to The Royal Horticultural Society Colour Chart. The actual color of Red Delano is not represented in The R.H.S. Colour Chart, and the values given are those believed closest to the actual color of Red Delano. The color values were determined on plant material grown as a pinched spray pot mum in Salinas, Calif. on Apr. 1, 1991.

Classification:

*Botanical.*—*Dendranthema grandiflora* cv. Red Delano.

*Commercial.*—Flat decorative disbud pot mum.

INFLORESCENCE

A. Capitulum:

*Form.*—Flat.

*Type.*—Decorative.

*Diameter across face.*—110 to 127 mm when fully opened.

B. Corolla of ray florets:

*Color (general tonality from a distance of three meters).*—Dark red.

*Color (upper surface).*—Closest to 185A to 185B, with inner ray florets closest to 59A.

*Color (under surface).*—Closest to 185C.

*Shape.*—Flat, oblong.

C. Corolla of disc florets:

*Color (mature).*—9A.

*Color (immature).*—Yellow, overlaid with 144C.

D. Reproductive organs:

*Androecium.*—Present on disc florets only; no pollen.

*Gynoecium.*—Present on both ray and disc florets.

PLANT

A. General appearance:

*Height.*—23 to 25 cm when grown as a pinched pot mum with 15 to 16 long days prior to start of short days and with 2 applications of 2500 ppm B-9 SP.

*Branching pattern.*—Spreading and prolific, with 4 to 5 laterals after pinch.

B. Foliage:

*Color (upper surface).*—147A.

*Color (under surface).*—147B.

*Shape.*—Lobed and slightly serrated.

I claim:

1. A new and distinct Chrysanthemum plant named Red Delano, as described and illustrated.

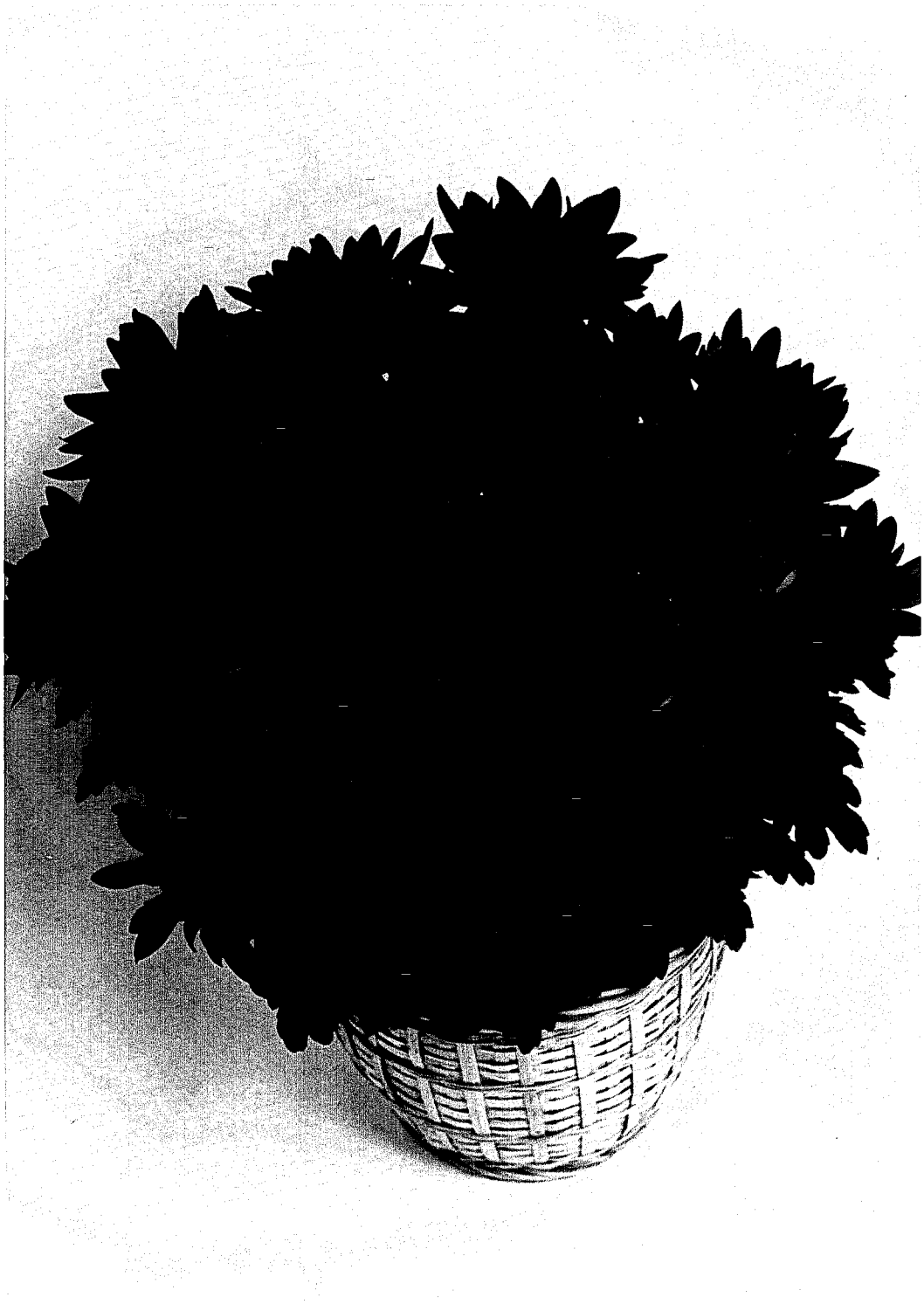

* * * * *